United States Patent
Batdorf

(10) Patent No.: US 6,897,191 B2
(45) Date of Patent: May 24, 2005

(54) DISINFECTING, ANTIMICROBIAL SEALING COMPOSITIONS AND METHODS OF USING THE SAME

(75) Inventor: Vernon H. Batdorf, Minneapolis, MN (US)

(73) Assignee: Specialty Construction Brands, Inc., St. Paul, MN (US)

( * ) Notice: Subject to any disclaimer, the term of this patent is extended or adjusted under 35 U.S.C. 154(b) by 211 days.

(21) Appl. No.: 10/427,693

(22) Filed: Apr. 30, 2003

(65) Prior Publication Data

US 2004/0219128 A1 Nov. 4, 2004

(51) Int. Cl.$^7$ .............................. C11D 3/48; C11D 3/37
(52) U.S. Cl. .................. 510/382; 510/131; 510/199; 510/319; 510/384; 510/388; 510/391; 510/475; 510/504
(58) Field of Search ................................ 510/131, 199, 510/319, 382, 384, 388, 391, 475, 504

(56) References Cited

U.S. PATENT DOCUMENTS

| | | | |
|---|---|---|---|
| 4,783,340 A | | 11/1988 | McDonell et al. |
| 4,883,828 A | * | 11/1989 | Oakes et al. ............. 514/772.4 |
| 4,929,454 A | | 5/1990 | Findlay et al. |
| 4,950,685 A | | 8/1990 | Ward |
| 4,999,386 A | * | 3/1991 | Oakes et al. ............... 523/122 |
| 5,049,383 A | | 9/1991 | Huth et al. |
| 5,061,485 A | * | 10/1991 | Oakes et al. ............... 514/643 |
| 5,154,920 A | | 10/1992 | Flesher et al. |
| 5,421,898 A | | 6/1995 | Cavanagh |
| 5,453,275 A | | 9/1995 | Terry et al. |
| 5,540,920 A | | 7/1996 | Vinopal et al. |
| 5,559,155 A | | 9/1996 | Walker |
| 5,585,407 A | | 12/1996 | Patel et al. |
| 5,587,407 A | | 12/1996 | Terry et al. |
| 5,635,192 A | | 6/1997 | Terry et al. |
| 5,639,464 A | | 6/1997 | Terry et al. |
| 5,776,960 A | | 7/1998 | Oppong et al. |
| 6,008,236 A | | 12/1999 | Oppong et al. |
| 6,017,561 A | | 1/2000 | Zhou et al. |
| 6,042,877 A | | 3/2000 | Lyon et al. |
| 6,242,526 B1 | | 6/2001 | Siddiqui et al. |
| 6,248,343 B1 | * | 6/2001 | Jampani et al. ............. 424/405 |
| 6,294,186 B1 | * | 9/2001 | Beerse et al. ............... 424/405 |
| 6,299,520 B1 | | 10/2001 | Cheyne, III |
| 6,464,764 B1 | | 10/2002 | Lichtenberg et al. |
| 6,482,392 B1 | | 11/2002 | Zhou et al. |
| 6,492,445 B2 | | 12/2002 | Siddiqui et al. |
| 2003/0055010 A1 | | 3/2003 | De Haan |

FOREIGN PATENT DOCUMENTS

| | | | |
|---|---|---|---|
| EP | 616015 | * | 9/1994 |
| EP | 0 616 015 A2 | | 9/1994 |
| EP | 0 937 812 A2 | | 8/1999 |
| WO | WO 97/06675 | | 2/1997 |
| WO | WO 98/05206 | | 2/1998 |
| WO | WO 99/59410 A1 | | 11/1999 |
| WO | WO 01/00021 | | 1/2001 |
| WO | WO 01/17357 | | 3/2001 |
| WO | WO 02/15693 | | 2/2002 |
| WO | WO 03/024217 | | 3/2003 |
| WO | 2004008851 | * | 1/2004 |
| WO | 2004/008851 A1 | | 1/2004 |

* cited by examiner

*Primary Examiner*—Charles Boyer

(57) ABSTRACT

The present invention relates to novel compositions for disinfecting and sealing a substrate, while also providing the surface with long-term fungicidal protection. Due to this unique and advantageous combination of capabilities, the composition finds particular utility in the construction industry, where it may advantageously be employed to treat a wide variety of construction articles.

21 Claims, No Drawings

DISINFECTING, ANTIMICROBIAL SEALING COMPOSITIONS AND METHODS OF USING THE SAME

FIELD OF THE INVENTION

The present invention relates to novel compositions for disinfecting a substrate, while also providing the substrate with long-term fungicidal protection. Additionally, the composition can act as a sealant in order to help prevent the airborne migration of any debris that may be present on the surface of the substrate, as may include any microorganisms killed by the composition. Due to this unique combination of capabilities, the composition finds utility in many applications and industries and is particularly useful in the construction industry, where it may advantageously be employed to treat a wide variety of construction articles, especially those comprising porous materials.

BACKGROUND OF THE INVENTION

Many compositions for disinfecting surfaces are known, as are compositions capable of acting as antimicrobials or fungicides. Typically, these disinfecting compositions kill fungus or bacteria present on the surface to which they are applied, but tend to do so effectively only at the time of application. That is, known disinfectants tend to be 'one-time kill' compositions, and once dried via evaporation, will not provide any long-term protection from future contamination of the surface. Similarly, known long-acting antimicrobials or fungicides typically do not provide immediate disinfection of a contaminated surface, rather providing protection only after some delay, e.g., after they have dried upon the treated surface.

Such compositions are used, oftentimes necessarily, in many industries under a variety of conditions. For example, the use of such compositions is pervasive in the construction industry where large quantities of a wide variety of materials may be stored, shipped and/or used at any given job site. These materials, both prior to and after having been constructed into the desired final form, may be subjected to a wide variety of conditions, and in fact, often must effectively weather wide fluctuations in temperature, light, and moisture in order to be suitable for this use.

For the health and safety of the users of construction materials, these materials would desirably be, and remain, substantially free of contamination by microorganisms. While known disinfectants may be effective to disinfect the surface of a construction article, their effect is not long lasting. Known anti-microbial agents, on the other hand, are limited in that they are not effective to disinfect a surface, rather acting to protect the surface from microbial infestation once dried thereupon. In order to achieve both effects, a disinfectant must be first applied to effectively clean the surface, followed by application of an antimicrobial agent in order to provide long-term protection from re-growth or re-infestation by microorganisms.

Desirably, compositions would be available that could provide both an initial disinfecting effect, while also providing long-term antimicrobial activity. It would be further advantageous if such a composition could entrap any debris present on the surface of the material to prevent any airborne migration of the same, particularly in light of health issues such as allergies and other respiratory problems that may be associated therewith. Any such compositions would clearly provide great benefit to any of a wide variety of applications and industries, and in particular, would be expected to find particularly beneficial application in the construction industry.

SUMMARY OF THE INVENTION

The present invention relates to disinfecting, antimicrobial sealing compositions, as well as methods of disinfecting and sealing a substrate, while also providing the substrate with long-term antimicrobial effect. More particularly, the present invention provides compositions comprising a unique combination of ingredients that are selected and formulated into a composition in such a way that the beneficial effect as may be attributed to or contributed by each of the ingredients, is not only substantially maintained, but may in fact, be synergistically enhanced. As such, the present compositions are capable of providing a combination of benefits that previously could be attained in many instances only via the application of at least two compositions and/or by performing at least two steps.

In a first aspect then, the present invention provides a disinfecting, antimicrobial, sealing composition. The composition comprises a hydrophobic, water-insoluble, film-forming polymer, at least a first disinfecting agent and at least a first antimicrobial agent. Advantageously, the composition may be water-based and substantially free of organic solvent. Because of the hydrophobic, water-insoluble nature of the polymer, interaction between the polymer and the desirably water-soluble disinfecting agent, will be minimized so that the activity of these compounds may be substantially unaffected, regardless of the ionic nature of the polymer. In certain embodiments, the polymer may desirably be nonionic or cationic to further minimize any possibility of interaction with preferred disinfecting or antimicrobial agents. The composition can be formulated with varying viscosity and/or percent solids so as to be capable of at least minimally penetrating a surface, or, so as to be capable of coating a surface with a film. Whether formulated to be capable of penetrating or coating, a film so formed can be substantially water and abrasion resistant so that the sealing and antimicrobial actions of the composition can extend for long periods of time, e.g., at least 48 hours, preferably at least about 28 days, more preferably up to about 2 years.

The present compositions find utility in a wide variety of industries for application to a wide variety of substrates. However, because of the wide variety of materials used therein, as well as the diverse array of conditions under which the materials are manufactured, stored, shipped and used, the construction industry is but one example of an industry that may be particularly benefited via use of the present composition.

In yet another aspect, the present invention provides construction articles having had a disinfecting antimicrobial sealing composition applied to at least a portion thereof wherein the composition comprises at least a first hydrophobic, water-insoluble polymer, at least a first disinfecting agent, and at least a first antimicrobial agent. Once applied, the compositions can form a dried film that further can be substantially tack-free, tough and water-resistant so that the construction articles are easily handled, shipped, and stored. The compositions are very stable and can be applied by any method at temperatures ranging from ambient to 40° F. to any substrate, whether damp or dry.

As a result, and in a further aspect, the present invention provides a method of disinfecting and sealing at least a portion of a construction article, and further of providing long-term antimicrobial activity thereto. The method comprises applying a disinfecting, antimicrobial, sealing composition to the construction article. The disinfecting, antimicrobial, sealing composition comprises at least a first hydrophobic, water-insoluble, film-forming polymer, at least a first disinfecting agent, and at least a first antimicrobial agent. Once applied, the composition can act to disinfect the article, and forms a film that can act to seal any debris, as may include microorganisms killed by the composition, that may be present to the surface of the article. The formed film also seals the antimicrobial agent to the article, thus providing the article with long-term protection against re-infestation or re-growth of microorganisms.

DETAILED DESCRIPTION OF EMBODIMENTS OF THE INVENTION

The embodiments of the present invention described below are not intended to be exhaustive or to limit the invention to the particular embodiments disclosed in the following detailed description. Rather, the embodiments are described so that others skilled in the art can understand the principles and practices of the present invention.

Unless noted otherwise, the following terms, as used herein, have the following meanings. Such terms may be explained in greater detail later in the specification. The phrases "long-term antimicrobial agent" or "long-term antimicrobial effect" is meant to an antimicrobial capable of, or the effect of, delivering at least about 48 hours of prevention of substantial microbial re-infestation and growth, as can be measured by treating an inoculated specimen with the present compositions, incubating the specimens in a humidified atmosphere, reinoculating every 24 hours, and testing for reinfestation and growth for the desired period of time thereafter. Further, the phrase "disinfecting agent" is meant to indicate a disinfecting agent that provides at least a 5 log reduction of microbes in 10 minutes as may be measured by AOAC 961.02. The phrase "hydrophobic polymer" is meant to indicate a polymer that lacks affinity for water, being only minimally soluble in water, if at all. As such, a hydrophobic polymer may include polymers completely incapable of dissolving in water or only minimally capable of dissolving in water, i.e., up to only about 500 ppm. The term "water-insoluble" is meant to include substances having a solubility in water of less than about 5000 ppm, or even less than about 2000 ppm. "Water-insoluble" can also advantageously include substances having a solubility water of less than about 500 ppm. The phrase "weight percent", and the abbreviation thereof "wt %", are meant to indicate weight percent as based upon the weight of the entire composition. The phrase "zone of inhibition" is meant to indicate a horizontal or vertical distance of at least about 2 mm from the antimicrobial agent, at least about 3 mm from the antimicrobial agent, or even at least 4 mm from the antimicrobial agent, within which the antimicrobial agent will exhibit the stated efficacy.

The present invention provides disinfecting, antimicrobial and sealing compositions. Due to their unique combination of ingredients, the inventive compositions are capable of providing a unique combination of benefits in a single composition, that may be applied in a single application. More particularly, the composition can act to disinfect a substrate, entrap any debris, such as dead microorganisms as may have been killed by the composition, and to provide long-term antimicrobial efficacy to the substrate via the application of the present compositions in a single application. Since the compositions are capable of disinfecting a substrate and sealing any debris thereto, the substrate need not be scraped, washed, cleaned or otherwise prepared prior to application of the present composition, and, once applied, no further treatment need be carried out to ready the substrate for further finishing. The compositions are further advantageously water-based and are yet surprisingly substantially water and abrasion resistant, so that once applied and dried upon a substrate, the composition may remain at the application site for an extended period of time thereby providing sealing and antimicrobial effects for a lengthened period of time.

More particularly, the present compositions include an admixture of ingredients comprising a hydrophobic, film-forming water-insoluble polymer, at least a first disinfecting agent, and at least a first antimicrobial agent. Any disinfecting agent showing good biocidal activity can be employed in the present compositions, although any such disinfecting agent will desirably be capable of forming a uniform, stable admixture with the other ingredients of the composition so that the composition, in turn, can exhibit good coating uniformity, and efficacy, while also desirably being substantially storage stable. The disinfecting agent advantageously can act to disinfect a surface or substrate to which it is applied, i.e., by weakening, killing, neutralizing or otherwise impairing a substantial portion, if not substantially all, of the microorganisms that the composition contacts. Desirably, the disinfecting agent will be capable of weakening, killing, neutralizing or otherwise impairing at least about 99.999% or the organisms, to result in at least about a 5 log reduction in the same. As used herein, the term microorganism is meant to include one or more of, bacteria, fungus, mold, yeast, algae, spores and combinations thereof, etc.

Suitable disinfecting agents thus include, but are not limited to, primary, secondary and tertiary amines, as well as salts and quaternary ammonium salts thereof. Examples of primary amines suitable for use in the present composition include $C_{8-18}$-alkylamines, $N$—($C_{8-18}$-alkyl)ethylenediamines, $N$—($C_{8-18}$-alkyl)propylenediamines, N,N-bis(2-aminoethyl)-$C_{8-18}$-alkylamines. Suitable secondary amines include, but are not limited to methyl- or ethyl-$C_{8-18}$-alkylamines. Tertiary amines suitable for use in the present compositions include, for example, dimethyl($C_{8-18}$- alkyl)amines. Useful salts of these may include, e.g., halides, such as bromides and chlorides, as well as salts of organic acids. Suitable quaternary ammonium salts include dimethyldi($C_{8-18}$ alkyl)ammonium halides, dimethyldi($C_{8-18}$ alkyl) ammonium salts of organic acids, trimethyl($C_{8-18}$ alkyl)ammonium halides, trimethyl($C_{8-18}$ alkyl) ammonium salts of organic acids, dimethyl($C_{8-18}$ alkyl)benzylammonium halides, dimethyl($C_{8-18}$ alkyl) ammonium salts of organic acids, 1,1'-dimethyl-4,4'-bipyridinium halides, and di($C_{8-18}$ alkyl)methyl-polyoxyethylammonium salts of organic acids. Organic acids, as mentioned herein, include formic acid, acetic acid, propionic acid, butyric acid, or isobutyric acid, as well as hydroxyl acids such as glycolic acid, lactic acid, malic acid or tartaric acid; and sulphonic acids, such as methanesulphonic acid, benzene-sulphonic acid or toluenesulphonic acid. Of these quaternary ammonium salts are considered particularly advantageous due to their efficacy and relatively high safety and/or environmentally compatible characteristics of these compounds.

The at least one disinfecting agent will desirably be used in the present composition in an amount such that the composition, once applied to a substrate, can weaken, kill, neutralize, or otherwise impair substantially all of the microorganisms present. This effective amount will vary depending upon the particular disinfecting agent chosen, including the activity level thereof when in solution, and those of ordinary skill in the art are readily able to determine such amounts using routine experimentation. Very generally speaking then, the at least one disinfecting agent will be present in the composition in amounts ranging from about 0.01 wt % active to about 10 wt % active, or from about 0.05 wt % to about 7 wt % active, based upon the total weight of the composition. Often times, from about 0.1 wt % to about 0.5 wt % active of at least one disinfecting agent will be suitable.

Prior to the present invention, the formulation of certain of these disinfecting agents into effective compositions with a film-forming polymer and/or antimicrobial had been difficult due to the reactivity of these compounds with desired film-forming polymers or antimicrobial agents. That is, many film-forming polymers may either require a solvent in order to be cast as a film, or are water-based and hydrophilic. In the former case, there may be applications in which the use of solvents is undesirable and in the case of the latter, the polymer may interact undesirably with the disinfecting agent when brought into close proximity therewith as may occur if both are in solution together. Further, hydrophilic polymers would not only be water-soluble, but also tend to bind and absorb water, and as a result may not be water and/or abrasion resistant when dried into a film.

It has now been surprisingly discovered that the above-identified disinfecting agents may be provided in a water-based composition with a film-forming polymer without substantial undue loss of activity if the polymer is at least hydrophobic and water-insoluble. In such a composition, the two components would likely remain phase-separated, thereby minimizing any interaction therebetween. In addition to this advantageous minimized interaction, the water-insoluble character of the polymer may also provide the further advantage of forming a substantially water and/or abrasion resistant film upon drying.

In certain embodiments, the hydrophobic, water-insoluble polymer may also be provided so as to be of substantially similar ionic character to the disinfecting agent so that the polymer and disinfecting agent may be repelled from one another by electrostatic forces. For example, in those preferred embodiments of the invention wherein the disinfecting agent is a quaternary ammonium salt, the film-forming polymer may advantageously be provided in the form of a substantially nonionic or substantially cationic emulsion or dispersion.

Examples of water-insoluble, hydrophobic, film-forming polymers that are also nonionic or cationic and suitable for inclusion in the present compositions include, but are not limited to, styrene acrylic copolymers, such as those commercially available under the trade names Acronol S702 (BASF, Aktiengesellschaft, Mount Olive, N.J.), PD-330 (H.B. Fuller Company, St. Paul, Minn.), and Res 1018, 1019 and 4040 (Rohm & Haas Company, Philadelphia Pa.); acrylic homopolymers such as commercially available under the trade names Ucar 376 and 351 (Dow Chemical, Midland, Mich.) and Res 3077 (Rohm & Haas); styrene butadiene block copolymers, such as those commercially available under the trade name DL313NA (Dow Chemical); ethylene vinyl acetate copolymers, such as those commercially available under the trade names Airflex 400/A405/460 (Air Products and Chemicals, Inc., Allentown, Pa.) and Elvace 1875 (Reichhold Inc., Durham, N.C.); polyvinyl acetate homopolymers, such as those commercially available under the trade names PD-316 (H.B. Fuller Company) and Airflex XX220/230 (Air Products and Chemicals, Inc.); acrylate-acrylonitrile copolymers, such as those commercially available under the trade name Synthemul (various grades, Reichhold Inc.); vinyl acetate-vinyl chloride ethylene copolymers, such as those commercially available under the trade name Airflex 728 (Air Products and Chemicals, Inc.); ethylene vinyl acetate butyl acrylate terpolymers, such as those commercially available under the trade names Airflex 809 and Airflex 811 (Air Products and Chemicals, Inc.); butadiene-acrylonitrile copolymers, such as those commercially available under the trade name Tylac, various grades (Reichhold Inc.); vinyl acrylic-vinyl chloride copolymers, such as those commercially available under the trade name Haloflex 563 (Zeneca Resins, Wilmington, Mass.); polychloroprene polymers and copolymers, such as those commercially available under the trade name DuPont Neoprene latex 115 (E.I. du Pont de Nemours and Company, Wilmington, Del.); and mixtures thereof.

Although in certain embodiments the water-insoluble, hydrophobic polymer is substantially nonionic or cationic so that it may be repelled from the preferred cationic disinfecting agents, the hydrophobic polymer may also be anionic if desired. In these embodiments of the invention, the amount of preferred disinfecting agent will simply be increased, so that the desired disinfecting effect will yet be seen. Interaction between an anionic polymer and preferred disinfecting agents would be expected to be stoichiometric in nature, and as such, one of ordinary skill in the art would be readily capable of calculating the ratio of disinfecting agent to anionic film-forming polymer required to at least achieve similar efficacy as when a substantially cationic or nonionic polymer is employed.

Suitable anionic, hydrophobic, water-insoluble film-forming polymers thus include, but are not limited to, styrene acrylic copolymers, such as those commercially available under the trade name PD-600 (BASF); acrylic homopolymers, such as those commercially available under the trade names PD-431, PD-449, PD-483 and PD-2049F (H.B. Fuller Company); vinyl acrylic copolymers, such as those commercially available under the trade names PD-119 and PD-124 (H.B. Fuller Company); styrene butadiene block copolymers such as those commercially available under the trade names NM-565 and ND-422 (BASF) and Rovene 6105 (Mallard Creek Polymers Inc., Charlotte, N.C.); vinylidene chloride-acrylic-vinyl-chloride copolymers, such as those commercially available under the trade names Vycar 660×1 4 and Vycar 460×46 (Noveon Inc., Cleveleand, Ohio); water-borne urethane polymers such as Neo Rez R-962, 967 and 972 (Zeneca Resins); and mixtures of these.

The hydrophobic, water-insoluble, film-forming polymer can be utilized in any desired amount, and the amount utilized will depend at least in part on the particular polymer chosen, as well as the properties of the formulated composition. Generally speaking, the polymer can be present in the composition in amounts ranging from about 1 wt % to about 90 wt %, or from about 10 wt % to about 80 wt % based upon the total weight of the composition. Often times, amounts of from about 15 wt % to about 75 wt % of the film-forming polymer, based upon the total weight of the composition, will be suitable.

Advantageously, the present compositions can be formulated having a variety of viscosities and a wide range of percent solids depending upon the desired application of the composition. In certain applications, it may be desired that the composition, once applied, provide a coating on the substrate as may be desired in instances where the substrate is substantially non-porous. In others it may be desired that the composition be capable of penetrating at least a portion of the surface of a substrate so that disinfecting and antimicrobial effect may be seen below the surface of a substrate. In the former case, a relatively viscous solution perhaps having a relatively high percent solids content would preferably be formulated, and in the latter, a lower viscosity solution, having a lower percent solids would be more appropriate.

Bearing these considerations in mind, and in those embodiments of the invention wherein a composition capable of being applied as a coating is desired (as may be the case when the substrate is non-porous, e.g. glass), the composition may be formulated to have a Brookfield viscosity of from about 5000 cps to about 100,000 cps, as measured at 75° F. and 20 RPM shear with a 5, 6 or 7 spindle. A particularly suitable composition for such applications may have a viscosity of at least about 15,000 cps, or at least about 30,000 cps, or even at least about 50,000 cps. Similarly, the solids content of such a composition may be at least about 55.0 wt %, or up to about 75.0 wt %.

On the other hand, in those embodiments of the invention wherein the composition may desirably penetrate at least a portion of the surface of a substrate to which it is applied, as may be particularly desirable in porous substrates permeable to water and thus susceptible to microbial infestation and growth, e.g. wood, a suitable composition will have a Brookfield viscosity of from about 1 cps to about 5000 cps. A particularly suitable composition for such applications may have a viscosity of less than about 1000 cps, or even less than about 500 cps. The solids content of such a composition may be less than about 30 wt %, less than 20 wt %, or even less than about 10 wt %.

The present composition further desirably includes at least a first antimicrobial agent. Any desired antimicrobial agent may be employed, so long as it is capable of forming a uniform, stable admixture with the other components of the composition. Desirably, the antimicrobial agent will be one that is capable of weakening, killing, neutralizing or otherwise impairing a microorganism upon direct contact therewith, or upon contact within a zone of inhibition surrounding the antimicrobial agent. Once the composition is applied and dried, it can form a film that entraps not only any debris present on the surface, but also the antimicrobial agent. Due at least in part to the water and abrasion resistance of the film, and also the long-term effect of the antimicrobial agents, the substrate can thus be provided with long-term antimicrobial activity, i.e., for up to at least about 48 hours, preferably for up to at least about 28 days, and more preferably for up to at least about 2 years, as can be measured according to ASTM D5590.

Particularly advantageous antimicrobial agents desirably have a low water solubility so that the antimicrobial agent will not substantially leach out of the composition under wet conditions once it has been applied to a substrate and dried to form a film, further assisting in the long-term efficacy of the antimicrobial agent. That is, in addition to the water-resistant nature of the film, the low water solubility of the antimicrobial agents can act to provide the film with long-term antimicrobial efficacy. Antimicrobial agents having a water solubility of from about 0.10 ppm (parts per million) to about 0.5% are expected to exhibit this capability, and may advantageously be utilized in the present compositions.

Examples of suitable antimicrobial agents thus include, but are not limited to, zinc 2-pyridinethiol-1-oxide, sodium 2-pyridinethiol-1-oxide, sodium borate, zinc borate, barium metaborate, calcium borate, iodo alkynyl alkyl carbamate, diiodomethyl-p-tolyl sulfone, 2-4-thiazolyl-benximidazole, 4,5-dichloro-2-n-octyl-4-isothiazolin-3-one, 2,4,4,-trichloro-2-hydroxy-diphenyl-ether, zinc dimethyldithiocarbamate, zinc 2-mercaptobenzothiazole, potassium n-hydroxymethyl-n-methyldithiocarbamate, sodium 2-mercaptobenzothiazole, 5-hydroxymethoxymethyl-1-aza-3,7-dioxa bicyclooctane, 2,3,5,6-tetra-chloro-4-pyridine, zinc 2-pyridinethiol-1-oxide, N-trichloromethylthiophthalimide, tetrachloroisophthalonitrile, including salts of any of these, or a mixture of any of these.

Of these, those with a relatively small particle size and/or that require relatively lesser amounts to be effective are advantageously utilized in compositions desirably capable of penetrating below the surface of at least a portion of the substrate. From the above list, zinc 2-pyridinethiol-1-oxide, sodium 2-pyridinethiol-1-oxide, iodo alkynyl alkyl carbamate, 2,3,5,6-tetra-chloro-4-pyridine, and zinc 2-pyridinethiol-1-oxide are examples of antimicrobial agents suitable for use in these applications. Those having a larger particle size, and/or requiring relatively larger amounts to be effective, e.g., sodium borate, zinc borate, barium metaborate and calcium borate, are well suited for use in applications wherein the composition is desirably applied as a coating.

The at least one antimicrobial agent will desirably be used in the present composition in an amount such that the composition, once applied to a substrate and dried, can weaken, kill, neutralize or otherwise impair the growth of microorganisms. This effective amount will vary depending upon the particular antimicrobial agent chosen, and those of ordinary skill in the art are readily able to determine such amounts using routine experimentation. Very generally speaking then, the antimicrobial agent may be present in the composition in amounts ranging from about 0.01 wt % to about 10.0 wt % active, or from about 0.1 wt % to about 7 wt % active, or even from about 1 wt % to about 5 wt % active, based upon the total weight of the composition.

The present compositions may include any other ingredients as may be desired, e.g., to increase the processability, stability, efficacy, coatability, etc., thereof. Examples of such ingredients that may optionally be used in the present composition include, but are not limited to, wetting agents, dispersing aids, thickeners, surfactants, pigments, defoaming agents, coalescing agents, fillers, reinforcing agents, adhesion promoters, plasticizers, flow control agents, ultraviolet absorbing agents, antistatic agents, emulsifiers, antioxidants, UV stabilizers, or combinations of these. Zinc oxide is but one particular example of an additive desirably added to the present compositions for many applications as it can not only provide coloring to the compositions, but may also provide the compositions with fungistatic activity. The amounts of any such additives to be included in the present compositions will depend upon the particular additive chosen, but generally speaking such additives are typically utilized in amounts ranging from about 0.01 wt % to about 15 wt %, based upon the total weight of the composition.

Beneficially, the compositions of the present invention may desirably be formulated either as dispersions or emulsions. The present compositions are further desirably free of environmentally hazardous heavy metal materials, e.g., arsenic, mercury, lead, tin and copper. The pH of the compositions is not critical, and the composition can be formulated without considerable regard thereto. Generally speaking then, compositions according to the present invention may have pH values ranging from about 2 to about 11, more preferably, from about 3 to about 10, most preferably from about 5 to about 8.

The admixtures may be water-based admixtures, and/or may comprise one or more other solvents. Water-based systems, substantially free of organic solvent, may be particularly advantageous inasmuch as the presence or use of volatile organic solvents may present safety concerns in some environments or to some users. In fact, inasmuch as the present compositions may effectively seal debris, such as mold or mold spores, to a surface they are expected to provide particular benefit to users of the compositions that suffer from allergies to the same. Allergy sufferers, or others exhibiting sensitivity to mold or other microorganisms often also suffer from associated respiratory difficulties, up to and including asthma. Such individuals often exhibit sensitivity to strong odors, including perfumes, smoke, pollution, smog, cleansers, and solvents and their choices of and exposure to, such items is desirably, or even necessarily limited. Water-based compositions according to the present invention are not only free from solvent odor, but also, are substantially free of any odor thereby rendering their use by, or on substrates near such individuals, non-offensive, and thus in fact beneficial.

Compositions according to the present invention are simply prepared by combining the ingredients thereof to form a substantially uniform admixture. As such, the ingredients may be combined by any known method using equipment conventional in the manufacture of the same, including any of a Cowles Dissolver, a Hockmeyer Mixer, a horizontal ribbon mixer, and the like.

Due to the unique combination of capabilities of the present compositions, they are advantageously applied to a wide variety of substrates and find ability in a wide variety of industries. Thus, the use of the present compositions is not particularly restricted, and the compositions may be applied to any substrate desirably disinfected, sealed and imparted with long-term antimicrobial effect whether substantially porous or non-porous in nature. As used herein, "substantially porous material" is meant to indicate one that is permeable by liquids or one that admits absorption of liquids via interstices, crevices, cracks, breaks, or other spaces between portions of substrate, which may either be closely set and minute, such as the pores in wood, or widely set, large spaces, such as in a loosely woven cloth. Examples of substantially porous materials include paper products, sponges, fiber products, woven and non-woven sheeting or fabric, plaster, wood, wood by-products, some decorative laminates, foam, bricks, stone, adhesives etc., while examples of substantially non-porous materials may include ceramics, glass, metal, polymer sheets or films and the like.

Due to the wide variance of conditions under which they may be manufactured, handled, stored, shipped and utilized, construction articles may find particular benefit in having the present compositions applied thereto. More particularly, these materials are often manufactured, shipped, stored and used under an extremely wide range of temperature, moisture and light conditions, including long periods of storage and use substantially, if not totally, exposed to the elements. As such, the present invention also provides construction articles having applied to at least a portion thereof a composition according to the present invention. Advantageously, construction articles having had the present compositions applied to at least a portion thereof can be exposed to the elements for several weeks, months or even years, and yet remain substantially free of microbial growth.

The present composition can provide some benefit to any construction article to which it is applied. Non-limiting examples of construction articles formed at least in part with substantially porous materials may thus include, but are not limited to, lumber, plywood, roofing shingles, concrete blocks, drywall, grout, concrete, insulation, wall coverings, carpeting, felt, carpet pad, moulding, clay roofing tile, plaster, ceiling tile. Examples of construction articles formed at least in part with substantially non-porous substrates include tile; hardware such as door handles, hinges, cabinet and drawer pulls and the like; light fixtures; plumbing fixtures; windows and window frames. Clearly certain construction articles may comprise of both porous and non-porous materials, e.g., windows and window frames, and such construction articles are clearly considered to be within the scope of the present invention.

Porous construction articles are expected to find particular benefit in having the present composition applied thereto. That is, since these types of materials are susceptible to water penetration or absorption, they are particularly susceptible to microbial infestation and growth. Further, porous construction articles such as wood products and by products, including lumber plywood are commonly shipped to construction sites and stored in contact with the ground and otherwise exposed to the elements. The present compositions are not only water-resistant, but also can provide long-term, penetrating antimicrobial effect, thereby assisting these articles in surviving these conditions. This may be critical to the structural integrity of such porous construction articles, and thus application of the present compositions to porous construction articles, and lumber in particular, is expected to prove particularly advantageous.

The compositions of the present invention may be applied to the desired substrate, preferably a construction article, by any known method. Suitable methods of application include, but are not limited to, spraying, rolling, dip coating, painting, pressure-assisted spraying, or combinations of these. In fact, this flexibility is yet another advantage of the present compositions, i.e., special equipment is not required for the application or drying thereof, and thus they are readily and easily applied in manufacturing settings, construction settings, or post-construction, i.e., as by a homeowner. The present invention thus also provides a method of disinfecting and sealing at least a portion of a construction article, and further of providing long-term antimicrobial activity to at least the disinfected and sealed portion. More specifically, the method comprises applying the present compositions to at least a portion of the construction article. The portion of the construction article so treated is thus substantially disinfected, has any debris that may have been present sealed thereto, and is imparted with a long-term antimicrobial effect. As such, the composition can be applied during the manufacture of the construction article to provide a pretreated construction article, may be applied to construction articles at a job site, or can be applied to completed construction that may have become contamination or infected.

EXAMPLES

Test Procedures

The following test procedures are suitable for use in the following examples:

Antimicrobial efficacy will be tested according to ASTM D-5590 Standard Test Method for Determining the Resistance of Paint Films and Related Coatings to Fungal Defacement by Accelerated Four-Week Agar Plate Assay.

Disinfecting efficacy will be tested according to AOAC Official Method 961.02 for Germicidal Spray Products as Disinfectants.

Viscosity will be tested at 20 RPM, 77° F. (25° C.) using a Brookfield viscometer on specimen aged in sealed container at ambient conditions for up to 12 months.

Example 1

An antimicrobial composition will be prepared by combining and blending uniformly 68.49 wt % water, 0.20 wt %

Natrasol 250 HHR, (cellulosic thickener, Hercules-Aqualon, Wilmington, Del.), 0.02 wt % water-soluble dye (red), 0.10 wt % Igepal CO-710, (nonionic surfactant, Rhodia, Inc. Brunswick, N.J.), 0.07 wt % Surfynol 104H, (nonionic surfactant, Air Products and Chemicals, Inc.), 2.00 wt % dipropylene glycol butyl ether (wetting agent, Lyondell Chemical, Houston, Tex.), 0.02 wt % fragrance (Alpine Aromatics, Inc. Piscataway, N.J.), 1.20 wt % Amical Flowable (40% active) (Dow Chemical) diiodomethyl p-tolyl sulfone, (antimicrobial agent, Dow Chemical, Houston, Tex.), 0.70 wt % zinc 2-pyridinethiol-1-oxide (48% active) (Arch Chemical, Cheshire, Conn.), 0.01 wt % defoamer (Dow Corning Corp. Midland, Mich.), 0.17 wt % Bardac® 205M (50% active) (disinfectant, Lonza, Inc. Fair Lawn, N.J.) and 27.00 wt % vinyl acetate-ethylene emulsion polymer (55% solids) (Air Products and Chemicals, Inc.).

The resultant composition is expected to have low-odor, a pH value of about 6 to about 8, a Brookfield viscosity of about 60 to about 120 cps, a solids content of about 16.2 wt %±1.0%, and a weight/gallon of about 8.5 lbs±0.1 lbs. The composition, when tested according to AOAC 961.02, is expected to show a 5 log reduction in 10 minutes, and when tested according to ASTM D-5590 on wood (pine, fir, oak and birch) and drywall paper facing, is expected to show zero growth rating at 200–500 ft$^2$/gallon.

Example 2

A composition according to the present invention will be prepared according to Example 1 except that 0.70 wt % IPBC-40 (40% active) (3-iodo-2-propnyl butyl carbamate, antimicrobial agent, Arch Chemical) will be used in place of zinc 2-pyridinethiol-1-oxide The composition is expected to have low odor, to show 5 log reduction in 10 minutes according to AOAC 961.02, and 0 growth rating according to ASTM D-5590.

Example 3

A composition according to the present invention will be prepared according to Example 2 except that 0.70 wt % Rozone 2000 (4,5-dichloro-2-n-octyl-4-isothiazolin-3-one, antimicrobial agent, Rohm & Hass, Philadelphia, Pa.) will be used in place of IPBC-40.

The composition is expected to have low odor, to show 5 log reduction in 10 minutes according to AOAC 961.02, and 0 growth rating according to ASTM D-5590.

Example 4

A composition embodying features of the present invention will be prepared according to Example 2 except that 0.70 wt % Irgaguard B 1000 (2,4,4-trichloro-2-hydroxy-diphenyl-ether, antimicrobial agent, Ciba Specialty Chemicals, Tarrytown, N.Y.) will be used in place of IPBC-40.

The composition is expected to have low odor, to show 5 log reduction in 10 minutes according to AOAC 961.02, and 0 growth rating according to ASTM D-5590.

Example 5

A composition embodying features of the present invention will be prepared by combining and blending uniformly 67.15 wt % water, 0.10 wt % Igepal CO-710, (nonionic surfactant), 0.05 wt % Surfynol 104H, (nonionic surfactant), 1.50 wt % propylene glycol (wetting agent), 0.4 wt % IPBC-40 (40% active), 0.40 wt % zinc 2-pyridinethiol-1-oxide (48% active), 0.40 wt % Bardac® 205M (50% active), and 30.00 wt % vinyl acetate-ethylene emulsion polymer (55% solids).

The composition is expected to have low odor, a pH value of about 6 to about 8, a Brookfield viscosity of about 60 to about 120 cps, a solids content of about 16.2 wt %±1.0%, and a weight/gallon of about 8.5 lbs±0.1 lbs. The composition is further expected to show 5 log reduction in 10 minutes according to AOAC 961.02, and 0 growth rating according to ASTM D-5590 when tested on wood and drywall paper facing at 100–160 ft$^2$/gallon.

Example 6

A composition embodying features of the present invention will be prepared according to Example 1 except that 27 wt % WD-4047 (urethane dispersion, H.B. Fuller Company) will be used in place of vinyl acetate ethylene emulsion polymer.

The composition is expected to have low odor, to show 5 log reduction in 10 minutes according to AOAC 961.02, and 0 growth rating according to ASTM D-5590. This composition is also expected to be flexible and/or thin enough once dried to be useful on fabric or paper substrates.

Example 7

Compositions embodying features of the present invention will be prepared according to Example 1 except that 27 wt % Witcobond W-245, W-281 or A-100 (urethane dispersions, Crompton Co., Middleburg, Conn.) will be used in place of vinyl acetate ethylene emulsion polymer to form three separate compositions according to the present invention.

The compositions are expected to have low odor, to show 5 log reduction in 10 minutes according to AOAC 961.02, and 0 growth rating according to ASTM D-5590. This composition is also expected to be flexible and/or thin enough once dried to be useful on fabric or paper substrates.

Example 8

Compositions embodying features of the present invention will be prepared according to Example 1 except that 27 wt % Bayhydral PR240 or PR435 (urethane dispersion, Bayer Coatings Group, Pittsburg, Pa.) will be used in place of vinyl acetate ethylene emulsion polymer to form two separate compositions according to the present invention.

The compositions are expected to have low odor, to show 5 log reduction in 10 minutes according to AOAC 961.02, and 0 growth rating according to ASTM D-5590. These compositions are also expected to be flexible and/or thin enough once dried to be useful on fabric or paper substrates.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A disinfecting antimicrobial sealing composition comprising an admixture of ingredients comprising:

at least a first hydrophobic, water-insoluble, film-forming polymer;

up to about 5% of at least a first disinfecting agent which is a quaternary ammonium salt; and at least a first antimicrobial agent selected from the group consisting of zinc 2-pyridinethiol-1-oxide, sodium 2-pyridinethiol-1-oxide, sodium borate, zinc borate, barium metaborate, calcium borate, iodo alkynyl alkyl carbamate, diiodomethyl-p-tolyl sulfone, 2-4-thiazolyl-benzimidazole, 4,5-dichloro-2-n-octyl-4-isothiazolin-3-one, 2,4,4,-trichloro-2-hydroxy-diphenyl-ether, zinc dimethyldithiocarbamate, zinc 2-mercaptobenzothiazole, potassium n-hydroxymethyl-n-methyldithiocarbamate, sodium 2-mercaptobenzothiazole, 5-hydroxymethoxymethyl-1-aza-3,7-dioxa bicyclooctane, 2,3,5,6-tetra-chloro-4-pyridine, N-trichloromethylthiophthalimide, tetrachloroisophthalonitrile, including salts of any of these, or a mixture of any of these.

2. The composition of claim 1, wherein the admixture is water-based.

3. The composition of claim 1, wherein the admixture is substantially free of environmentally hazardous materials.

4. The composition of claim 3, wherein the admixture is substantially free of volatile solvent.

5. The composition of claim 3, wherein the admixture is substantially free of heavy metals.

6. The composition of claim 1, wherein the percent solids of the composition is from about 10% to about 70%.

7. The composition of claim 1, wherein the polymer is cationic or nonionic.

8. The composition of claim 7, wherein the first disinfecting agent is a quaternary ammonium salt and is present in an amount of up to about 1% by weight of the total composition.

9. The composition of claim 1, wherein the polymer is anionic.

10. The composition of claim 1, wherein the antimicrobial agent is present in an amount of from about 0.1% to about 4% by weight of the total composition.

11. The composition of claim 1, wherein the antimicrobial agent comprises one or more of a zinc 2-pyridinethiol-1-oxide, sodium 2-pyridinethiol-1-oxide, iodo alkynyl alkyl carbamate, diiodomethyl-p-tolyl sulfone, 2-4-thiazolyl-benximidazole, 4,5-dichloro-2-n-octyl-4-isothiazolin-3-one, 2,4,4,-trichloro-2-hydroxy-diphenyl-ether, including salts of any of these or a mixture of any of these.

12. A construction article having a disinfecting antimicrobial sealing composition applied to at least a portion thereof, wherein the composition includes an admixture of ingredients comprising:
    at least a first hydrophobic, water-insoluble, film-forming polymer;
    up to about 5% of at least a first disinfecting agent which is a quaternary ammonium salt; and
    at least a first antimicrobial agent selected from the group consisting of zinc 2-pyridinethiol-1-oxide, sodium 2-pyridinethiol -1-oxide, sodium borate, zinc borate,
    barium metaborate, calcium borate, iodo alkynyl alkyl carbamate, diiodomethyl-p-tolyl sulfone, 2-4-thiazolyl-benzimidazole, 4,5-dichloro-2-n-octyl-4-isothiazolin-3-one, 2,4,4,-trichloro-2-hydroxy-diphenyl-ether, zinc dimethyldithiocarbamate, zinc 2-mercaptobenzothiazole, potassium n-hydroxymethyl-n-methyldithiocarbamate, sodium 2-mercaptobenzothiazole, 5-hydroxymethoxymethyl-1-aza-3,7-dioxa bicyclooctane, 2,3,5,6-tetra-chloro-4-pyridine, N-trichloromethylthiophthalimide, tetrachloroisophthalonitrile, including salts of any of these, or a mixture of any of these.

13. The construction article of claim 12, wherein the antimicrobial agent comprises one or more of a zinc 2-pyridinethiol-1-oxide, sodium 2-pyridinethiol-1-oxide, iodo alkynyl alkyl carbamate, diiodomethyl-p-tolyl sulfone, 2-4-thiazolyl-benximidazole, 4,5-dichloro-2-n-octyl-4-isothiazolin-3-one, 2,4,4,-trichloro-2-hydroxy-diphenyl-ether, a salt of any of these or a mixture of any of these.

14. The construction article of claim 12, wherein the article comprises one or more of lumber, wallboard, concrete, cement block, ceiling tile, insulation or wall paneling.

15. A method of disinfecting and sealing at least a portion of a construction article, and further of providing long-term antimicrobial activity thereto comprising:
    applying a disinfecting, antimicrobial, sealing composition to the construction article including an admixture of ingredients comprising:
    at least a first hydrophobic, water-insoluble, film-forming polymer;
    up to about 5% of at least a first disinfecting agent which is a quaternary ammonium salt; and
    at least a first antimicrobial agent selected from the group consisting of zinc 2-pyridinethiol-1-oxide, sodium 2-pyridinethiol-1-oxide, sodium borate, zinc borate,
    barium metaborate, calcium borate, iodo alkynyl alkyl carbamate, diiodomethyl-p-tolyl sulfone, 2-4-thiazolyl-benzimidazole, 4,5-dichloro-2-n-octyl-4-isothiazolin-3-one, 2,4,4,-trichloro-2-hydroxy-diphenyl-ether, zinc dimethyldithiocarbamate, zinc 2-mercaptobenzothiazole, potassium n-hydroxymethyl-n-methyldithiocarbamate, sodium 2-mercaptobenzothiazole, 5-hydroxymethoxymethyl-1-aza-3,7-dioxa bicyclooctane, 2,3,5,6-tetra-chloro-4-pyridine, N-trichloromethylthiophthalimide, tetrachloroisophthalonitrile, including salts of any of these, or a mixture of any of these; wherein upon applying the composition the portion is substantially disinfected, any debris present is substantially sealed to the surface of the portion, and the portion is provided with a long-term antimicrobial effect.

16. The method of claim 15, wherein the composition is applied by spraying, rolling, dip coating, painting, pressure-assisted spraying, or combinations of these.

17. The method of claim 15, wherein the construction article comprises lumber, plywood, roofing shingles, concrete blocks, drywall, grout, concrete, insulation, wall coverings, tile, carpeting, felt, carpet pad, hardware, light fixtures, plumbing fixtures, moulding, windows, clay roofing tile, plaster, ceiling tile or window frames.

18. The method of claim 15, wherein the composition provides at least a 5-log reduction in any microorganisms present on the construction article in about 10 minutes or less.

19. The method of claim 15, wherein the composition provides antimicrobial efficacy to the article for at least about 48 hours.

20. The method of claim 15, wherein the composition provides antimicrobial efficacy to the article for at least about 28 days.

21. The method of claim 15, wherein the composition provides antimicrobial efficacy to the article for at least about 2 years.

* * * * *